US00PP17998P3

(12) United States Plant Patent
Layt

(10) Patent No.: US PP17,998 P3
(45) Date of Patent: Sep. 11, 2007

(54) ***DIANELLA CAERULEA* PLANT NAMED 'DBB03'**

(50) Latin Name: *Dianella caerulea*
Varietal Denomination: DBB03

(75) Inventor: Todd Anthony Layt, New South Wales (AU)

(73) Assignee: Versascapes L.L.C., Mt. Pleasant, SC (US)

( * ) Notice: Subject to any disclaimer, the term of this patent is extended or adjusted under 35 U.S.C. 154(b) by 0 days.

(21) Appl. No.: 11/239,590

(22) Filed: Sep. 29, 2005

(65) Prior Publication Data

US 2006/0075535 P1 Apr. 6, 2006

Related U.S. Application Data

(60) Provisional application No. 60/614,654, filed on Sep. 30, 2004.

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS (Royal Horticultural Society Dictionary of Gardening, 1992, vol. II D–K, McMillan Press, London; Stockton Press, New York, p. 49–50).*
Layt: "*Dianella caerulea* blue flax lily 'DBB03,'" *Plant Varieties Journal* 16(4): 121 (Feb. 6, 2004).
Layt; "*Dianella caerulea* blue flax lily 'DBB03,'" *Plant Varieties Journal* 17 (1): 600–602 (Apr. 28, 2004).
Australian Government, IP Australia, Plant Breeder's Rights; Database entry for Australian Plant Breeders Right Application No. 2003/291; Variety 'DBB03' http://pbr.i-paustralia.optus.com.au/docs/2003291.doc.

* cited by examiner

*Primary Examiner*—Anne Marie Grunberg
*Assistant Examiner*—Georgia Helmer
(74) *Attorney, Agent, or Firm*—Myers Bigel Sibley & Sajovec, PA

(57) ABSTRACT

'DBB03' is a distinctive variety of *Dianella caerulea,* which is characterized by the combination of its open growth, a blue-green foliage, pale blue flowers, slightly spreading and semi-compact growth habit, and an absence of canes, which is unusual for a *Dianella caerulea,* particularly when compared to the 'Sydney Ecotype'. 'DBB03' is also less prone to falling over than the parent type.

2 Drawing Sheets

RELATED APPLICATION INFORMATION

This application claims the benefit of U.S. Provisional Application Ser. No. 60/614,654, filed Sep. 30, 2004, the disclosure of which is incorporated herein by reference in its entirety.

Latin name of the genus and species: The Latin name of the novel variety disclosed herein is *Dianella caerulea.*

Variety denomination: The inventive variety of *Dianella caerulea* disclosed herein has been given the varietal denomination 'DBB03'.

BACKGROUND OF THE INVENTION

The present invention relates to a new and distinct perennial Blue Flax Lilly variety of *Dianella caerulea,* which has been given the varietal denomination of 'DBB03'. The market class for 'DBB03' is that of an ornamental grass-like plant. 'DBB03' is intended for use in landscaping and as a decorative grass-like plant.

An application for plant breeders' rights for variety 'DBB03' has been filed with the Australian Plant Breeders' Rights Office, and was first gazetted in the Plant Varieties Journal in October 2003 under Application No. 2003/291.

Parentage: The *Dianella caerulea* variety 'DBB03' was first discovered in October 1996 in an Australian nursery in Clarendon, New South Wales after an extensive breeding program. The parent plant, 'Sydney Ecotype' (unpatented), is characterized by a tall plant height, a medium plant density, medium length aerial stems and a yellow-green leaf colour.

In 1995, *Dianella* species were grown together in an open bed covering approximately 250 square meters of area. They were grown in groups of species and ecotypes including *Dianella caerulea* collected from the Sydney area (*Dianella caerulea* 'Sydney Ecotype'), and other regions. The other *Dianella* species present were *longifolia, revoluta* and *tasmanica.* The plants were open pollinated with possible assisted pollination from general shaking of flower stems onto each other.

Seeds were collected and sown from the 'Sydney Ecotype' plants in December 1995. Approximately 30,000 plants were grown. In October 1996, using the selection criteria of bluish leaf colour, compact habit and absence of aerial stems (canes), a single plant was identified as having these characteristics. This plant was selected, potted into a 140 mm pot for further evaluation, and named 'DBB03'.

The female parent of 'DBB03' was *Dianella caerulea* 'Sydney Ecotype', and 'DBB03' has been identified as a *Dianella caerulea;* however, it is noted that 'DBB03' has a similar colour and shares several similar growth habits with some of the *Dianella longifolia* that were used in the open pollination breeding program. For these reasons, it is possible that the male parent of 'DBB03' was a *Dianella longifolia.*

Asexual reproduction. 'DBB03' was first asexually propagated by vegetative division in April 1997 in the state of New South Wales, Australia. 'DBB03' was asexually reproduced again during November 1997 and April 1998 and confirmed to be stable in character. The distinctive characteristics of the inventive variety, 'DBB03', have remained stable and true to type from generation to generation through successive cycles of asexual reproduction including vegetative division and micropropagation.

SUMMARY OF THE INVENTION

'DBB03' is a distinctive variety of *Dianella caerulea,* which is characterized by the combination of its open growth, a blue-green foliage, pale blue flowers, slightly spreading and semi-compact growth habit, and an absence of canes, which is unusual for a *Dianella caerulea,* particularly when compared to the 'Sydney Ecotype'. 'DBB03' is also less prone to falling over than the parent type.

BRIEF DESCRIPTION OF THE FIGURES

The photographs in the drawings were made using conventional techniques and show the colours as true as reasonably possible by conventional photography. Colours in the photographs may differ slightly from the colour values cited in the detailed botanical description, which accurately describe the colours of the new *Dianella caerulea.*

BOTANICAL DESCRIPTION OF THE PLANT

The following is a detailed botanical description of a new and distinct variety of a *Dianella caerulea* ornamental grass-like plant known as 'DBB03'. The descriptions disclosed herein are based upon observations of the plant grown in 140 mm nursery pots and field plots in New South Wales, Australia. The plants were approximately 12-months-old at the time of observation. All colours cited herein refer to The Royal Horticultural Society Colour Chart (The Royal Horticultural Society, London, 2001 edition).

Those skilled in the art will appreciate that certain characteristics will vary with older or, conversely, younger plants. 'DBB03' has not been observed under all possible environmental conditions. Where dimensions, sizes, colours and other characteristics are given, it is to be understood that such characteristics are approximations or averages set forth as accurately as practicable. The phenotype of the variety may differ with variations in the environment such as season, temperature, light intensity, day length, cultural conditions and the like.

Figure 1:
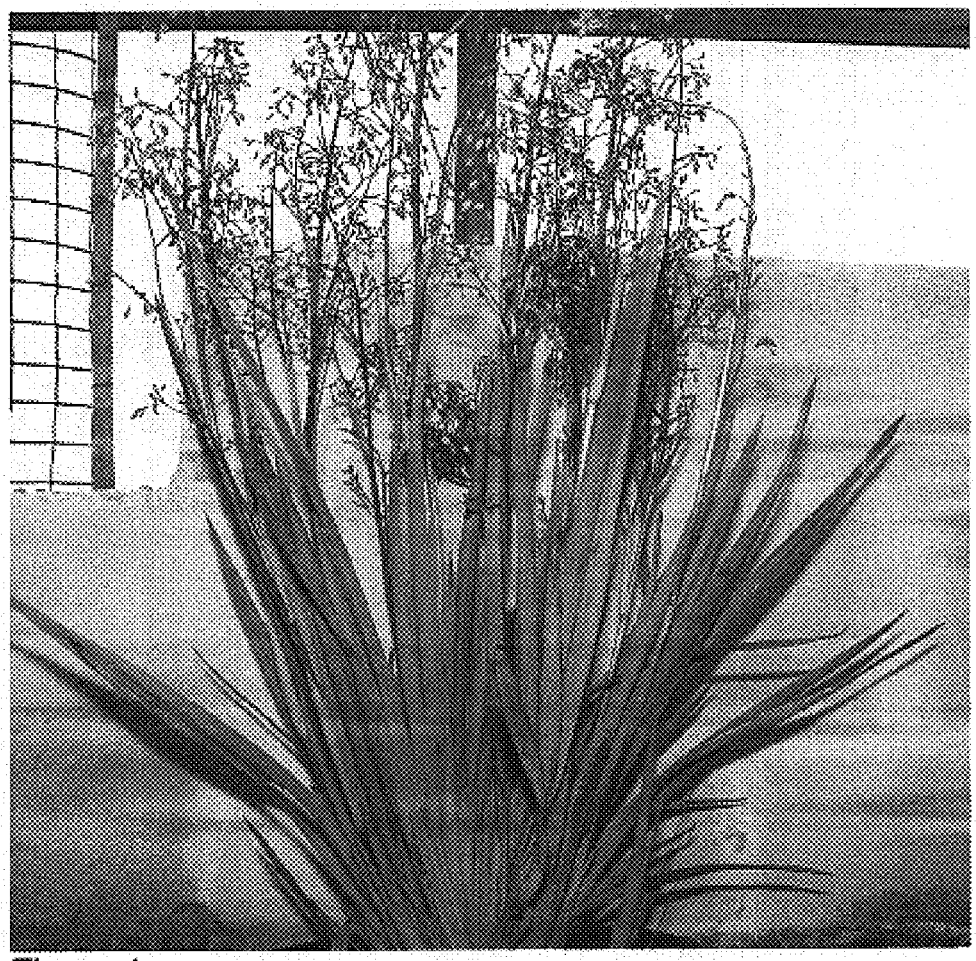
FIG. 1 shows a 'DBB03' plant and illustrates the absence of canes and tall flower spike height as compared with other *Dianella caerulea.*
Figure 2:
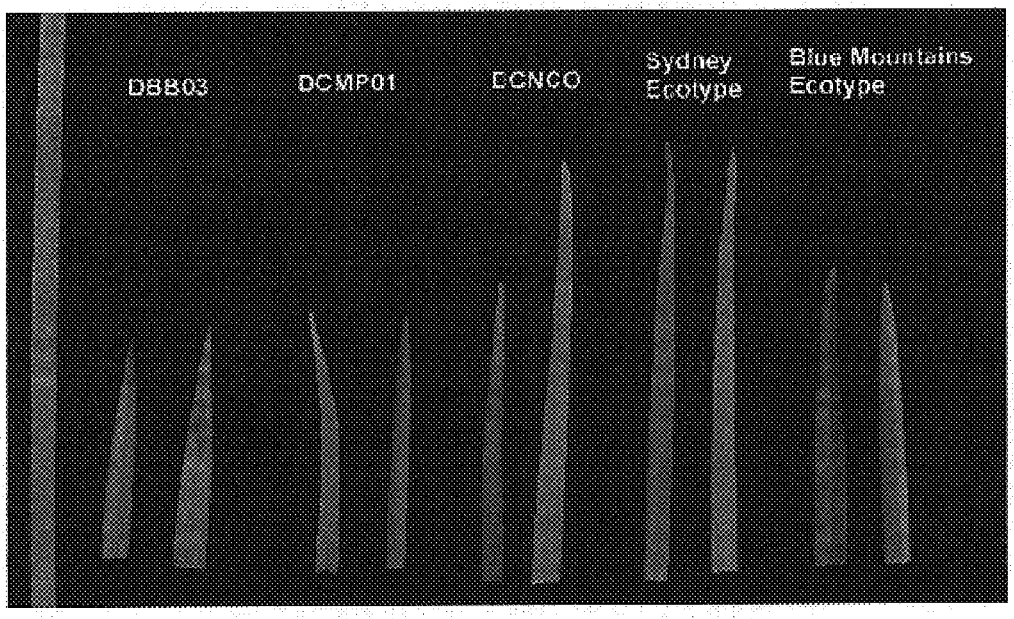
FIG. 2 shows the variation in leaf width and glaucosity among the five *Dianella caerullea* varieties included in the comparison study.

'DBB03' is a perennial *Dianella caerulea* plant, which was produced through an innovative breeding program. After its selection, 'DBB03' was asexually propagated by division and micropropagation. 'DBB03' has open growth, slightly spreading and a semi-compact growth habit, a short rhizome form, no canes, a blue-green foliage colour, a pale blue flower colour, and a reduced tendency to fall over at maturity. A botanical description of 'DBB03' and a comparison with other varieties of *Dianella caerulea* are provided below. A representative *Dianella caerulea* 'DBB03' plant is shown in FIG. 1.

Technical Description of the Variety.

Growth Habit. 'DBB03' is a short, rhizomatous plant forming a semi-compact tussock. Its growth habit is erect, its height is short (mean 23.4 cm) and the density of its shoots is strong.

Stem. Length of internodes is short (less than 10 mm). The Sydney ecotype has internode length which is long (greater than 20 mmm) creating long aerial stem length (also known as canes).

Foliage. Leaf attitude is erect to semi-erect, leaf width medium (mean 14.9 mm), upper side colour with waxiness removed yellow-green (RHS 147A), upper side colour with waxiness retained greyed-green (RHS 189A), lower side colour with waxiness removed yellow-green (RHS 147A), upper side glaucosity strong, shape ligulate, apex acute, cross section concave, cross-sectional shape with midrib keeled, spines on margin absent, spines on lower side midrib absent.

Basal Sheath. Colour greyed-green(RHS 189A) corresponding to the rest of the leaf: with waxiness removed yellow green (RHS 147A), with waxiness retained greyed-green (RHS 189A), anthocyanin colouration absent.

Inflorescence. The inflorescence (flower spike) is pale blue (approximately RHS 93D) with a longer length on average as compared with *Dianella caerulea* 'DCMP01' (U.S. Provisional application Ser. No. 60/614,658, filed Sep. 30, 2004, Australian Plant Breeders Rights Application No. 2003/292, received Oct. 8, 2003) and other *Dianella caerulea.* The flower spike is soft to the touch.

Environmental Tolerances. 'DBB03' has shown potential for shade tolerance. The winter hardiness of 'DBB03' is at least to −12 degrees Celsius. 'DBB03' has been observed to hold colour to −8 degrees Celsius. 'DBB03' has good colour retention in winter and normal drought tolerance, compared to the common form of this plant.

Disease Resistance and Susceptibility. 'DBB03' has excellent tolerance to pests and diseases and good resistance to root rot, which is a common problem in *Dianella caerulea.* Root rot is caused by the disease causing organism Phytophthora. Tolerance to pests can refer to no damage from snails, slugs, mites, aphids, whitefly, beetles, caterpillars and moths.

These features and other characteristics of the plant are apparent from the figures.

'DBB03' Compared to Other Varieties of *Dianella caerulea*

Grouping characteristics used to identify the most similar varieties of common knowledge to 'DBB03' included short height, and dense growth habit. Based on this, 'DCMP01' was selected as the most similar suitable comparator. The parent ('Sydney Ecotype') and another form from the Blue Mountains region of New South Wales , 'Blue Mountains Ecotype' (unpatented), were included in the trial. In addition, *D. caerulea* 'DCNCO' (U.S. Provisional application Ser. No. 60/614,804 filed Sep. 30, 2004; Australian Plant Breeders Rights Application No. 2003/293, received Oct. 8, 2003), which has a much taller plant height than 'DBB03', was also included in the comparative trial.

The comparative trial of *Dianella caerulea* 'DBB03' with other *D. caerulea* was conducted in open beds in Summer 2002 through Autumn 2003 in Clarendon, New South Wales, Australia. The plants for this trial were propagated from divisions and planted into 130 mm pots filled with soilless potting mix. Nutrition was maintained with slow release fertilizers and pest and disease treatments were applied as required. The plants did not flower during the trial. Trial design included fifteen pots of each variety arranged in a completely randomized design. Measurements were taken from ten plants at random with one sample taken per plant.

In comparing 'DBB03' with the other *Dianella caerulea* varieties, 'DBB03' has a more open growth habit than 'Sydney Ecotype', 'Blue Mountains Ecotype' and 'DCNC0'. 'DBB03' is characterized by a general absence of canes similar to 'DCNC0', whereas the 'Sydney Ecotype' has canes of typical length above the ground. Further, 'DBB03' has a taller flower spike height compared to 'DCNC0' and 'DCMP01', and the 'Sydney Ecotype' has a variable flower spike height. 'DBB03' and 'DCNC0' have pale blue flower colour, whereas 'DCMP01' has a deeper blue almost purplish flower colour, and the 'Sydney Ecotype' flower colour is variable. Further comparisons are presented in Table I.

TABLE I

Comparison of *Dianella caerulea* varieties.

| | 'DBB03' | 'DCMP01' | 'DCNCO' | 'Sydney Ecotype' | 'Blue Mountains Ecotype' |
|---|---|---|---|---|---|
| PLANT: GROWTH HABIT | erect | erect | erect | erect to semi-erect | semi-erect to erect |
| PLANT HEIGHT (cm) LSD (P ≦ 0.01) = 6.03 | | | | | |
| Mean | 23.4[c] | 24.6[c] | 65.6[a] | 63.0[a] | 49.4[b] |
| Std deviation | 2.2 | 2.6 | 5.0 | 5.5 | 8.5 |
| PLANT: DENSITY OF SHOOTS | strong | strong | medium-strong | medium | weak |
| STEM: INTER-NODE LENGTH | short | short | short | long | very long |
| LEAF: WIDTH (mm) LSD (P ≦ 0.01) = 1.97 | | | | | |
| Mean | 14.9[c] | 12.2[d] | 13.6[cd] | 17.1[b] | 22.2[a] |
| Std deviation | 2.1 | 0.6 | 0.8 | 0.9 | 2.9 |
| LEAF: FOLIAGE COLOUR - overall appearance of leaf | blue-green | yellow-green | yellow-green | yellow-green | yellow-green |
| LEAF: COLOUR - waxiness removed | | | | | |
| Upper side | 147A | 147A | 147B | 146B | ca 147A |

TABLE I-continued

Comparison of *Dianella caerulea* varieties.

| | 'DBB03' | 'DCMP01' | 'DCNCO' | 'Sydney Ecotype' | 'Blue Mountains Ecotype' |
|---|---|---|---|---|---|
| Lower side | 147A | 147B | 147B | 146B | 147B |
| LEAF: GLAUCOSITY | strong | weak | weak | weak | weak |
| LEAF: CROSS SECTION | concave | concave | slight concave | slight concave | concave |
| LEAF: PRESENCE OF SPINES ON MARGIN | absent | absent | present | present | present |
| LEAF: PROMINENCE OF SPINES ON MARGIN | n/a | n/a | medium | medium | very weak |
| LEAF: PRESENCE OF SPINES ON LOWER SIDE MIDRIB | absent | absent | present | present | present |
| LEAF: PROMINENCE OF SPINES ON LOWER SIDE MIDRIB | n/a | n/a | medium | medium | medium |
| BASAL SHEATH: COLOUR | blue-green | red-brown | red-brown | brown to red-brown | red to red-brown |
| BASAL SHEATH: INTENSITY OF ANTHOCYANIN COLOUR | absent | weak | medium | medium | strong |

Mean values followed by the same letter are not significantly different at P ≦ 0.01 according to an S-N-K test.

That which is claimed is:

1. A new and distinct variety of *Dianella caerulea* plant named 'DBB03', substantially as described and illustrated herein.

* * * * *